United States Patent [19]

Takahashi et al.

[11] Patent Number: 4,870,064
[45] Date of Patent: Sep. 26, 1989

[54] DIPROPARGYLOXYBENZENE COMPOUNDS AND THEIR PRODUCTION

[75] Inventors: Junya Takahashi, Hyogo; Shigeko Nakamura, both of Otsu, Japan

[73] Assignee: Sumitomo Chemical Company, Limited, Osaka, Japan

[21] Appl. No.: 80,488

[22] Filed: Jul. 29, 1987

[30] Foreign Application Priority Data

Aug. 12, 1986 [JP] Japan ............................ 61-188892
Aug. 19, 1986 [JP] Japan ............................ 61-193486
Sep. 9, 1986 [JP] Japan ............................ 61-212955
Nov. 7, 1986 [JP] Japan ............................ 61-266458

[51] Int. Cl.$^4$ ..................................... A01N 9/36
[52] U.S. Cl. ................................. 514/115; 514/365; 514/376; 514/389; 514/394; 514/531; 514/538; 514/720; 568/649
[58] Field of Search ............... 568/649; 514/115, 365, 514/376, 389, 394, 531, 538, 720

[56] References Cited

FOREIGN PATENT DOCUMENTS

132881 11/1984 European Pat. Off. .
0249567 12/1987 European Pat. Off. ............ 568/649

*Primary Examiner*—Ferris H. Lander
*Attorney, Agent, or Firm*—Birch, Stewart, Kolasch & Birch

[57] ABSTRACT

A compound of the formula:

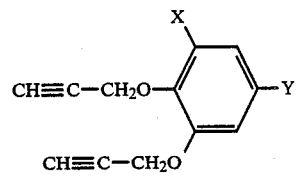

wherein X is a halogen atom and Y is a $C_1$–$C_4$ alkyl group, a $C_2$–$C_4$ alkenyl group, a $C_1$–$C_3$ alkoxy group, a $C_3$–$C_4$ alkenyloxy group, a $C_3$–$C_4$ alkynyloxy group, a $C_2$–$C_3$ alkenyl group substituted with phenyl, a $C_3$–$C_4$ alkenyloxy group substituted with halogen, a $C_1$–$C_3$ alkoxy group substituted with one member selected from the group consisting of halogen, $C_1$–$C_3$ alkoxy, $C_1$–$C_3$ alkanoyl, cyano, hydroxycarbonyl, $C_1$–$C_3$ alkylaminocarbonyl and phenyl, or a group of the formula: —$CH_2O$—$R^1$, —$CH$=$CH$—$R^2$, —$CH$=$N$—$R^3$ or —$CO$—$R^4$ in which $R^1$ is a $C_1$–$C_3$ alkyl group, a $C_3$–$C_4$ alkenyl group or a $C_3$–$C_4$ alkynyl group, $R^2$ is a cyano group, a methoxycarbonyl group or an acetyl group, $R^3$ is a dimethylamino group or a phenyl group and $R^4$ is a $C_1$–$C_2$ alkyl group, which is useful as a fungicidal agent against phytopathogenic fungi, particularly strains resistant to benzimidazole or thiophanate fungicides and/or cyclic imide fungicides.

8 Claims, No Drawings

DIPROPARGYLOXYBENZENE COMPOUNDS AND THEIR PRODUCTION

This invention relates to dipropargyloxybenzene compounds and their production.

Benzimidazole and thiophanate fungicides such as Benomyl (methyl 1-(butylcarbamoyl)benzimidazol-2-ylcarbamate), Fubelidazol (2-(2-furyl)benzimidazole, Thiabendazole (2-(4-thiazolyl)benzimidazole), Carbendazim (methyl benzimidazol-2-ylcarbamate), Thiophanate-methyl (1,2-bis(3-methoxycarbonyl-2-thioureido)-benzene), Thiophanate (1,2-bis(3-ethoxycarbonyl-2-thioureido)benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene are known to show an excellent fungicidal activity against various plant pathogenic fungi, and they have been widely used as agricultural fungicides since 1970. However, their continuous application over a long period of time provides phytopathogenic fungi with tolerance to them, whereby their plant disease-preventive effect is significantly lowered. Further, the fungi which developed tolerance to certain kinds of benzimidazole or thiophanate fungicides also show considerable tolerance to some other kinds of benzimidazole or thiophanate fungicides. Thus, they are likely to develop cross-tolerance. Therefore, if any material decrease of their plant disease-preventive effect in certain fields is observed, their application to such fields has to be discontinued. But, it is often observed that the density of drug-resistant organisms is not decreased even long after the discontinuation of the application. Although other kinds of fungicides have to be employed in such case, only few are as effective as benzimidazole or thiophanate fungicides in controlling various phytopathogenic fungi.

Cyclic imide fungicides such as Procymidone (3-(3',5'-dichlorophenyl)-1,2-dimethylcyclopropane-1,2-dicarboximide), Iprodione (3-(3',5'-dichlorophenyl)-1-isopropylcarbamoylimidazolidine-2,4-dione), Vinchlozolin (3-(3',5'-dichlorophenyl)-5-methyl-5-vinyloxazolidin-2,4-dione) and ethyl (RS)-3-(3',5'-dichlorophenyl)-5-methyl-2,4-dioxooxazolidine-5-carboxylate, which are effective against various plant diseases, particularly those caused by *Botrytis cinerea*, have the same defects as previously explained with respect to the benzimidazole or thiophanate fungicides.

As a result of a study seeking a new type of fungicide, it has now been found that dipropargyloxybenzene compounds of the formula

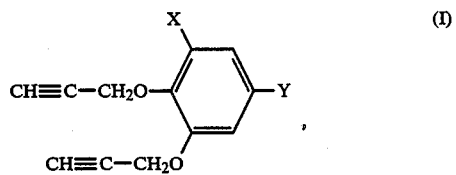

wherein X is a halogen atom and Y is a $C_1$–$C_4$ alkyl group, a $C_2$–$C_4$ alkenyl group, a $C_1$–$C_3$ alkoxy group, a $C_3$–$C_4$ alkenyloxy group, a $C_3$–$C_4$ alkynyloxy group, a $C_2$–$C_3$ alkenyl group substituted with phenyl, a $C_3$–$C_4$ alkenyloxy group substituted with halogen, a $C_1$–$C_3$ alkoxy group substituted with one member selected from the group consisting of halogen, $C_1$–$C_3$ alkoxy, $C_1$–$C_3$ alkanoyl, cyano, hydroxycarbonyl, $C_1$–$C_3$ alkylaminocarbonyl and phenyl, or a group of the formula: —$CH_2O$—$R^1$, —$CH$=$CH$—$R^2$, —$CH$=$N$—$R^3$ or —$CO$—$R^4$ in which $R^1$ is a $C_1$–$C_3$ alkyl group, a $C_3$–$C_4$ alkenyl group or a $C_3$–$C_4$ alkynyl group, $R^2$ is a cyano group, a methoxycarbonyl group or an acetyl group, $R^3$ is dimethylamino group or a phenyl group and $R^4$ is a $C_1$–$C_2$ alkyl group show an excellent fungicidal activity against plant pathogenic fungi which have developed resistance to benzimidazole, thiophanate and/or cyclic imide fungicides. It is notable that their fungicidal potency against the organisms tolerant to benzimidazole, thiophanate and/or cyclic imide fungicides (hereinafter referred to as "drug-resistant fungi" or "drug-resistant strains") is much higher than that against the organisms sensitive to benzimidazole, thiophanate and/or cyclic imide fungicides (hereinafter referred to as "drug-sensitive fungi" or "drug-sensitive strains").

The dipropargyloxybenzene compounds (I) are fungicidally effective against a wide scope of plant pathogenic fungi, of which examples are as follows: *Podosphaera leucotricha, Venturia inaequalis, Mycosphaerella pomi, Marssonina mali* and *Sclerotinia mali* of apple, *Phyllactinia kakicola* and *Gloeosporium kaki* of persimmon, *Cladosporium carpophilum* and *Phomopsis* sp. of peach, *Cerospora viticola, Uncinula necator, Elsinoe ampelina* and *Glomerella cingulata* of grape, *Cercospora beticola* of sugarbeet, *Cercospora arachidicola* and *Cercospora personata* of peanut, *Erysiphe graminis* f. sp. hordei, *Pseudocercosporella herpotrichoides* and *Fusarium nivale* of barley, *Erysiphe graminis* f. sp. tritici of wheat, *Sphaerotheca fuliginea* and *Cladosporium cucumerinum* of cucumber, *Cladosporium fulvum* of tomato, *Corynespora melongenae* of eggplant, *Sphaerotheca humuli, Fusarium oxysporum* f. sp. fragariae of strawberry, *Botrytis alli* of onion, *Cercospora apii* of cerely, *Phaeoisariopsis griseola* of kidney bean, *Erysiphe cichoracearum* of tobacco, *Diplocarpon rosae* of rose, *Elsinoe fawcetti, Penicillium italicum, Penicillium digitatum* of orange, *Botrytis cinera* of cucumber, eggplant, tomato, strawberry, pimiento, onion, lettuce, grape, orange, cyclamen, rose or hop, *Sclerotinia sclerotiorum* of cucumber, eggplant, pimiento, lettuce, celery, kidney bean, soybean, azuki bean, potato or sunflower, *Sclerotinia cinerea* of peach or cherry, *Mycosphaerella melonis* of cucumber or melon, etc. Namely, the dipropargyloxybenzene compounds (I) are highly effective in controlling the drug-resistant strains of said fungi. The dipropargyloxybenzene compounds (I) can also exert a significant antifungal activity against *Pyricularia oryzae, Pseudoperonospora cubensis, Plasmopara, viticola, Phytophthora infestans,* etc.

Advantageously, the dipropargyloxybenzene compounds (I) are low in toxicity and have a few detrimental effects on mammals, fishes and so on. Also, they may be applied to agricultural fields without causing any material toxicity to important crop plants.

From the viewpoint of exertion of fungicidal properties, notable are those of the formula:

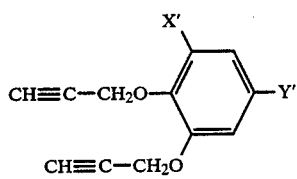

wherein X' is a chlorine atom and Y' is a $C_1$–$C_3$ alkyl group, a $C_2$–$C_3$ alkenyl group, a $C_1$–$C_3$ alkoxy group, a $C_3$ alkynyloxy group, a halo($C_2$)alkoxy group, a halo($C_3$)alkenyloxy group, a methylcarbonylmethoxy group, a 2-cyanovinyl group, a phenyliminomethyl group or a group of the formula: —$CH_2O$—$R^{1'}$ in which $R^{1'}$ is a methyl group, a $C_3$ alkenyl group or a $C_3$ alkynyl group.

Particularly notable are those of the formula:

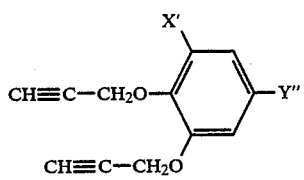

wherein X' is a chlorine atom and Y" is a methyl group, an ethyl group, a methoxy group, an ethoxy group, a propyloxy group, a vinyl group, a propargyloxy group, a 2-fluoroethoxy group, a methoxymethoxy group, a 3-chloro-2-propenyl group, a 2-chloro-2-propenyl group, a methylcarbonylmethoxy group, a 2-cyanovinyl group or a phenyliminomethyl group.

The dipropargyloxybenzene compounds (I) can be prepared by various procedures, of which typical ones are shown below:

Procedure (a):

A compound of the formula:

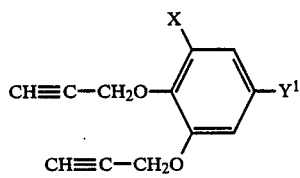

wherein X is as defined above and $Y^1$ is a $C_1$–$C_4$ alkyl group, a $C_2$–$C_4$ alkenyl group, a $C_1$–$C_3$ alkoxy group, a $C_3$–$C_4$ alkenyloxy group, a $C_3$–$C_4$ alkynyloxy group, a $C_2$–$C_3$ alkenyl group substituted with phenyl, a $C_3$–$C_4$ alkenyloxy group substituted with halogen, a $C_1$–$C_3$ alkoxy group substituted with one member selected from the group consisting of halogen, $C_1$–$C_3$ alkoxy, $C_1$–$C_3$ alkanoyl, cyano, hydroxycarbonyl, $C_1$–$C_3$ alkylaminocarbonyl and phenyl, or a group of the formula: —CO—$R^4$ in which $R^4$ is a $C_1$–$C_2$ alkyl group is prepared by reacting a compound of the formula:

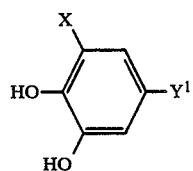

wherein X and $Y^1$ are each as defined above with propargyl halide.

The reaction is usually carried out in an inert solvent (e.g. N,N-dimethylformamide, tetrahydrofuran, acetonitrile, chloroform, toluene, water, their mixtures) in the presence of a base at a temperature from 0° to 120° C., preferably from room temperature to 90° C., within about 30 hours. Examples of the base are sodium hydride, triethylamine, pyridine, sodium hydroxide, potassium hydroxide, sodium carbonate, potassium carbonate, etc. A phase transfer catalyst (e.g. tetra-n-butylammonium bromide) may be used in the reaction, if desired.

The compound (II) is obtainable by demethylating a compound of the formula:

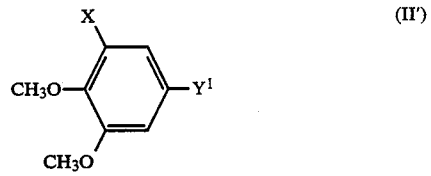

wherein X and $Y^1$ are each as defined above.

The reaction usually proceeds in an inert solvent (e.g. benzene, toluene, dichloromethane) in the presence of a demethylating agent (e.g. anhydrous aluminum chloride, boron tribromide, pyridine hydrochloride) at a temperature from −70° C. to a boiling point of the solvent within 30 hours.

The starting compound (II') is prepared according to the method as described in *Tappi* 1971, Vol. 54 (7), 1114–1121.

A typical example for preparation of the compound (II) is illustratively shown in the following example.

REFERENCE EXAMPLE 1

A solution of boron tribromide (3 ml) in dichloromethane (15 ml) was dropwise added to a solution of 3-chloro-4,5-dimethoxytoluene (1.5 g) in dichloromethane (75 ml) at −60° C., followed by stirring at room temperature overnight. The reaction mixture was poured into ice and extracted with dichloromethane. The extract was washed with water, dried over magnesium sulfate and concentrated under reduced pressure to give 3-chloro-5-methylcathecol (1.20 g).

$^1$H—NMR δ TMS (CDCl$_3$+DMSO-d$_6$) ppm: 6.52 (s, 2H), 6.00 (broad, 2H), 23.15 (s, 3H).

Procedure (b):

A compound of the formula:

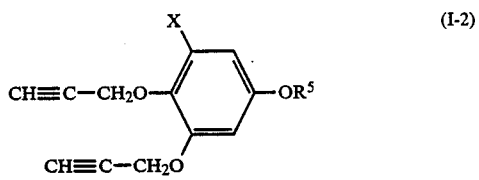

wherein X is as defined above and $R^5$ is a $C_1$–$C_3$ alkyl group, a $C_3$–$C_4$ alkenyl group, a $C_3$–$C_4$ alkynyl group, a $C_3$–$C_4$ alkenyl group substituted with halogen, a $C_1$–$C_3$ alkyl group substituted with one member selected from the group consisting of halogen, $C_1$–$C_3$ alkoxy, $C_1$–$C_3$ alkanoyl, cyano, hydroxycarbonyl, $C_1$–$C_3$ alkylaminocarbonyl and phenyl is prepared by reacting a compound of the formula:

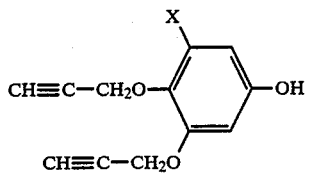

(III)

wherein X is as defined above with a compound of the formula: R⁵—Z in which R⁵ is as defined above and Z is a leaving group (e.g. halogen, mesyloxy, tosyloxy).

The reaction proceeds in the same manner as in Procedure (a).

The starting compound (III) is obtainable by hydrolyzing a compound of the formula:

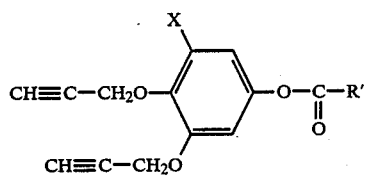

(III')

wherein X is as defined above and R' is a hydrogen atom or a $C_1$–$C_2$ alkyl group.

The hydrolysis is performed in water or an aqueous alcohol (e.g. methanol, ethanol) in the presence of a base (e.g. sodium hydroxide, triethylamine) from room temperature to the refluxing temperature of the reaction mixture within about 12 hours.

The compound (III') is obtainable by oxidation of a compound of the formula:

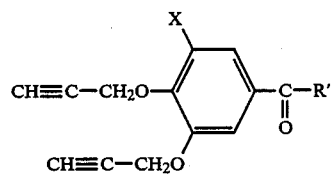

(III")

wherein X and R' are each as defined above.

The oxidation is carried out in a solvent (e.g. dichloromethane, chloroform, carbon tetrachloride) in the presence of an oxidizing agent (e.g. m-chloroperbenzoic acid, peracetic acid) from room temperature to the refluxing temperature of the reaction mixture.

The compound (III") is obtainable by reacting a compound of the formula:

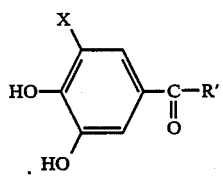

(III''')

wherein X and R' are each as defined above with propargyl halide.

The compound (III''') may be prepared according to the method as described in J. Chem. Soc., Perkin 1, 1015 (1973).

Typical examples for preparation of the compounds (III), (III'), (III") and (III''') are illustratively shown in the following examples.

REFERENCE EXAMPLE 2

Sodium hydride (2.69 g; 60% dispersion in mineral oil) was added to dimethylformamide (500 ml). To the mixture was added a solution of 3-chloro-4,5-dihydroxybenzaldehyde (11.6 g) in dimethylformamide (100 ml) at a temperature of 0° to 5° C., followed by stirring at room temperature for 1 hour. Propargyl bromide (8.00 g) was added thereto. The resultant mixture was heated at 90° C. for 5 minutes and cooled to 0° C., and sodium hydride (2.69 g) was added thereto. After the foaming ceased, propargyl bromide (8.00 g) was added to the reaction mixture. The resultant mixture was heated at 90° C. for 5 minutes, poured into ice-water and extracted with ethyl acetate. The extract was washed with aqueous potassium carbonate solution and water, dried over magnesium sulfate and concentrated under reduced pressure. The residue was subjected to alumina chromatography using toluene as an eluent to give 3-chloro-4,5-dipropargyloxybenzaldehyde (5.46 g). m.p. 64°–65° C.

REFERENCE EXAMPLE 3 m-Chloroperbenzoic acid (8.0 g) was added to a solution of 3-chloro-4,5-dipropargyloxybenzaldehyde (5.0 g) in dichloromethane (50 ml) at room temperature, and the resultant mixture was stirred overnight. After removal of the solid material by filtration, the filtrate was concentrated to give 3-chloro-4,5-dipropargyloxyphenylformate.

$^1$H—NMR δ TMS (CDCl₃) ppm: 8.21 (s, 1H), 6.80 (d, 1H), 6.85 (d, 1H), 4.72 (m, 4H), 2.55 (m, 2H).

The thus obtained crude 3-chloro-4,5-dipropargyloxyphenylformate was dissolved in a solution of potassium carbonate (10.0 g) in ethanol (50 ml) and water (50 ml), and the resulting mixture was stirred for 1 hour, poured into a mixture of aqueous hydrochloric acid and ice and extracted with ethyl acetate. The extract was washed with water, dried over magnesium sulfate and concentrated under reduced pressure. The residue was purified by silica gel column chromatography using chloroform as an eluent to give 3-chloro-4,5-dipropargyloxyphenol (3.3 g). $n_D^{22.0}$ 1.5580.

Procedure (c):

A compound of the formula:

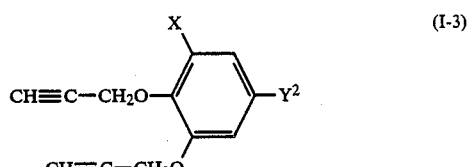

(I-3)

wherein X is as defined above and $Y^2$ is a $C_2$–$C_4$ alkenyl group, a $C_2$–$C_3$ alkenyl group substituted with phenyl or a group of the formula: —CH═CH—R² in which R² is as defined above is prepared by reacting a compound of the formula:

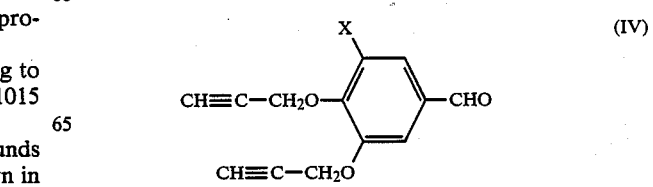

(IV)

wherein X is as defined above with either one of the compounds of the formulas: $(C_6H_5)_3—P^{\oplus}—R^6Z'$,

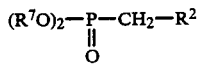

or $(C_6H_5)_3—P^{\oplus}—CH_2—R^2Z'$ in which $R^2$ is as defined above, $R^6$ is a $C_1$-$C_3$ alkyl group or a $C_1$-$C_2$ alkyl group substituted with phenyl, $R^7$ is a lower alkyl group and $Z'$ is a halogen atom.

The reaction is usually carried out in an inert solvent (e.g. N,N-dimethylformamide, tetrahydrofuran, diethyl ether, dioxane, acetonitrile, chloroform, toluene, water, their mixtures) in the presence of a base at a temperature from −70° to 50° C., preferably from −70° C. to room temperature, within about 30 hours. Examples of the base are n-butyl lithium, sodium hydride, triethylamine, pyridine, sodium hydroxide, potassium hydroxide, sodium carbonate, potassium carbonate, etc. A phase transfer catalyst (e.g. tetra-n-butylammonium bromide) may be used in the reaction, if desired.

Procedure (d):

A compound of the formula:

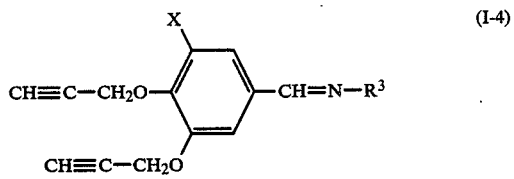
(I-4)

wherein X and $R^3$ are each as defined above is prepared by reacting the compound (IV) with 1,1-dimethylhydrazine or aniline.

The reaction is effected in a solvent (e.g. benzene, toluene, xylene, methanol, ethanol) in the presence or absence of a dehydrating gent (e.g. molecular sieve) and/or a catalyst (e.g. p-toluenesulfonic acid) at a temperature from room temperature to the refluxing temperature of the reaction mixture within about 24 hours.

Procedure (e):

A compound of the formula:

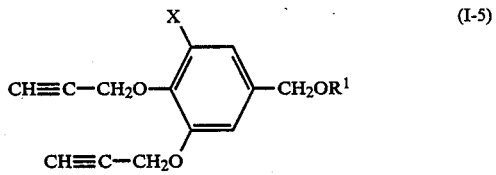
(I-5)

wherein X and $R^1$ are each as defined above is prepared by reacting a compound of the formula:

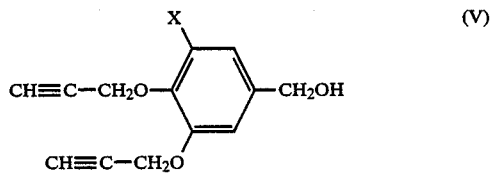
(V)

wherein X is as defined above with a compound of the formula: $R^1$—Z in which $R^1$ and Z are each as defined above.

The reaction proceeds in the same manner as in Procedure (a).

The compound (V) is obtained by reducing the compound (IV) in a solvent (e.g. water, methanol, ethanol, benzene, toluene, hexane, ethyl acetate, dioxane, tetrahydrofuran, their mixtures) in the presence of a reducing agent (e.g. sodium borohydride, lithium borohydride, lithium aluminum hydride, aluminum ethoxide, aluminum isopropoxide) at a temperature from −10° to 100° C. within about 12 hours.

A typical example for preparation of the compound (V) is illustratively shown in the following example.

REFERENCE EXAMPLE 4

3-Chloro-4,5-dipropargyloxybenzaldehyde (14.7 g) was added to a solution of sodium borohydride (3.6 g) in ethanol (150 ml) at a temperature below 30° C. After stirring at room temperature for 2 hours, the resultant mixture was poured into dilute hydrochloric acid under cooling and extracted with ethyl acetate. The extract was washed with water, dried over magnesium sulfate and concentrated under reduced pressure to give 3-chloro-4,5-dipropargyloxybenzyl alcohol (15.60 g)/. $n_D^{17.0}$ 1.5713.

Procedure (f):

A compound of the formula:

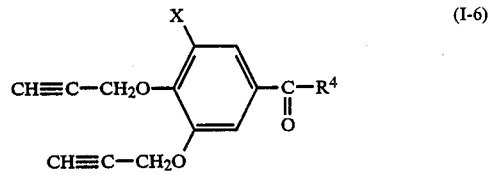
(I-6)

wherein X and $R^4$ are each as defined above is prepared by hydroxylation of a compound of the formula:

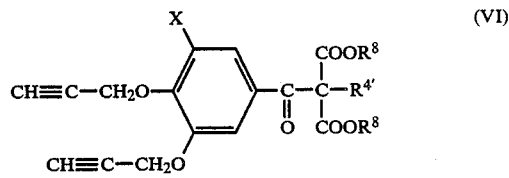
(VI)

wherein X is as defined above, $R^{4'}$ is a hydrogen atom or a methyl group and $R^8$ is a lower alkyl group, followed by decarboxylation.

The reaction is carried out in the presence of an acid (e.g. acetic acid, diluted hydrochloric acid, aqueous sulfuric acid, their mixtures) at a temperature from 50° C. to the refluxing temperature of the reaction mixture within about 20 hours.

The compound (VI) may be prepared by reacting a compound of the formula:

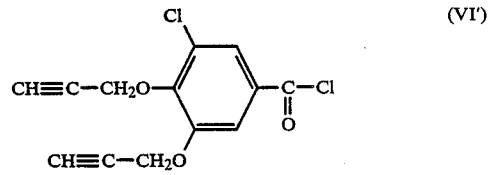
(VI')

with a compound of the formula: $R^4CH(COOR^8)_2$ wherein $R^4$ and $R^8$ are each defined above in the same manner as in Procedure (a).

The compound (VI') is obtained by reacting a compound of the formula:

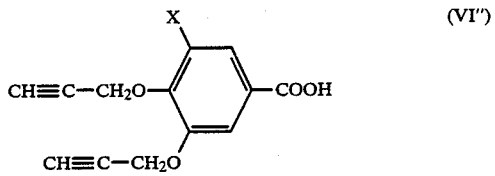

wherein X is as defined above with a halogenating agent (e.g. thionyl chloride, thionyl bromide, phosgene) in the absence or presence of an inert solvent (e.g. benzene, toluene, hexane, tetrahydrofuran, their mixtures) at a temperature from room temperature to the refluxing temperature of the reaction mixture within about 12 hours.

The compound (VI'') is prepared by oxidation of the corresponding aldehyde (VI). Examples of the oxidizing agent are Jones reagent, manganese dioxide, potassium permanganate, pyridinium chlorochromate, etc. The reaction is usually carried out in an inert solvent (e.g. water, acetone, benzene, toluene, hexane, dichloromethane, carbon tetrachloride, or their mixtures at a temperature of 0° to 100° C. within about 12 hours.

Typical examples for preparation of the compounds (VI), (VI') and (V''') are illustratively shown in the following examples.

REFERENCE EXAMPLE 5

Jones reagent (e.g. an aqueous sulfuric acid solution of chromium trioxide) was added to a solution of 3-chloro-4,5-dipropargyloxybenzaldehyde (18.0 g) in acetone (100 ml) under stirring at a temperature below 20° C. The addition was stopped when the reaction mixture became red, and stirring was continued at 20° C. for 1 hour. The reaction mixture was poured into ice-water containing ethanol (100 nl) and extracted with ethyl acetate. The extract was washed with water, dried over magnesium sulfate and concentrated under reduced pressure. The residue was washed with hexane to give 3-chloro-4,5-dipropargyloxybenzoic acid (16.2 g). m.p. 158°–159° C.

REFERENCE EXAMPLE 6

A mixture of 3-chloro-4,5-dipropargyloxybenzoic acid (10.7 g) and thionyl chloride (30 ml) was stirred under reflux for 1 hour. After cooling, the reaction mixture was evaporated under reduced pressure to give 3-chloro-4,5-dipropargyloxybenzoyl chloride in a quantitative yield.

IR (Nujol): 3275, 2100, 1740, 1140, 820 cm$^{-1}$.

NMR $\delta$ TMS (CDCl$_3$): 7.85 (d, 1H), 7.65 (d, 1H), 4.90 (d, 2H), 4.80 (d, 2H), 2.40–2.70 (2H).

REFERENCE EXAMPLE 7

Diethyl malonate (4.5 g) was combined with a mixture of sodium hydride (1.1 g; 60% dispersion in mineral oil) and tetrahydrofuran (100 ml) at room temperature, and the resultant mixture was stirred for 1 hour. 3-Chloro-4,5-dipropargyloxybenzoyl chloride (7.8 g) was added thereto, followed by stirring under reflux for 1 hour. The resultant mixture was poured into ice water and extracted with ethyl acetate. The extract was washed with water, dried over magnesium sulfate and concentrated under reduced pressure to give diethyl 3-chloro-4,5-dipropargyloxybenzoyl malonate.

NMR $\delta$ TMS (CDCl$_3$) ppm: 7.55 (s, 2H), 5.20 (s, 1H), 4.80 (d, 4H), 4.20 (q, 4H), 2.55 (t, 2H), 1.25 (t, 6H).

The compounds (I-3) and (I-4) can have cis- and trans-isomers and represent such cis- or trans-isomer, or their mixture, inclusively.

Some typical examples for preparation of the compound (I) are illustratively shown in the following examples.

EXAMPLE 1

Preparation of 3-chloro-4,5-dipropargyloxytoluene according to Procedure (a):

Sodium hydride (0.10 g; 60% dispersion in mineral oil) was added to dimethylformamide (30 ml). To the mixture was dropwise added a solution of 3-chloro-5-methyl catechol (0.40 g) in dimethylformamide (10 ml) at a temperature of 0° to 5° C., followed by stirring at room temperature for 1 hour. Propargyl bromide (0.35 g) was added thereto, and the resultant mixture was heated at 90° C. for 5 minutes and cooled to 0° C. Sodium hydride (0.10 g; 60% dispersion in mineral oil) was further added thereto. After the foaming ceased, propargyl bromide (0.35 g) was added to the reaction mixture, which was heated at 90° C. for 5 minutes, poured into ice-water and extracted with ethyl acetate. The extract was washed with potassium carbonate solution and water, dried over magnesium sulfate and concentrated under reduced pressure. The residue was purified by silica gel column chromatography using toluene as an eluent to give 3-chloro-4,5-dipropargyloxytoluene (0.45 g).

$^1$H—NMR $\delta$ TMS (CDCl$_3$) ppm: 6.70–6.90 (2H), 4.68 (d, 4H), 2.40–2.60 (2H), 2.25 (s, 3H).

EXAMPLE 2

Preparation of 1-chloro-2,3-dipropargyloxy-5-methoxybenzene according to Procedure (b):

Sodium hydride (0.32 g; 60% dispersion in mineral oil) was added to dimethylformamide (50 ml). To the mixture was added 3-chloro-4,5-propargyloxyphenol (1.9 g) at a temperature of 0° to 5° C., followed by stirring at room temperature for 1 hour. Iodomethane (1.50 g) was added thereto, and the resultant mixture was heated at 90° C. for 5 minutes, poured into ice-water and extracted with ethyl acetate. The extract was washed with potassium carbonate solution and water, dried over magnesium sulfate and concentrated under reduced pressure. The residue was purified by silica gel column chromatography using toluene as an eluent to give 1-chloro-2,3-dipropargyloxy-5-methoxybenzene (1.8 g).

$^1$H—NMR $\delta$ TMS (CDCl$_3$) ppm: 6.50 (s, 2H0, 4.60–4.80 (4H), 3.27 (s, 3H), 2.42–2.62 (2H).

EXAMPLE 3

Preparation of 1-(3-chloro-4,5-dipropargyloxyphenyl)butene according to Procedure (c):

n-Propyltriphenylphosphonium bromide (4.66 g) was dissolved in dry diethyl ether (50 ml), and n-butyl lithium (7.6 ml; 1.6N) was added thereto at 0° C. under nitrogen stream, followed by stirring at room temperature for 3 hours. A solution of 3-chloro-4,5-dipropargyloxybenzaldehyde (3.0 g) in dry diethyl ether (50 ml) was dropwise added to the resultant mixture, which was stirred at room temperature overnight, poured into ice-water and extracted with ethyl acetate. The extract was washed with water, dried over magnesium sulfate and concentrated under reduced pressure. The residue was purified by silica gel column chromatography using toluene as an eluent to give 1-(3-chloro-4,5-dipropargyloxyphenyl)butene (2.7 g). $n_D^{25.0}$ 1.5602.

EXAMPLE 4

Preparation of 2-(3-chloro-4,5-dipropargyloxyphenyl)acrylonitrile according to Procedure (c):

Diethyl cyanomethylphosphonate (1.42 g) was dissolved in dimethylformamide (50 ml), and sodium hydride (0.32 g; 60% dispersion in mineral oil) was added thereto at 0° C. under cooling. After the foaming ceased, 3-chloro-4,5-dipropargyloxybenzaldehyde (2.00 g) was added to the reaction mixture, which was stirred at room temperature overnight, poured into ice-water and extracted with ethyl acetate. The extract was washed with water, dried over magnesium sulfate and concentrated under reduced pressure. The residue was purified by silica gel column chromatography to give 2-(3-chloro-4,5-dipropargyloxyphenyl)acrylonitrile (1.85 g). m.p., 110°–111° C.

EXAMPLE 5

Preparation of N-(3-chloro-4,5-dipropargyloxybenzyliden)aniline according to Procedure (d):

A mixture of 3-chloro-4,5-dipropargyloxybenzaldehyde (1.00 g) and aniline (0.37 g) in benzene (30 ml) was stirred under reflux for 3 hours, followed by concentration under reduced pressure to give N-(3-chloro-4,5-dipropargyloxybenzyliden)aniline (1.30 g). $n_D^{23.0}$ 1.5890.

EXAMPLE 6

Preparation of 1-chloro-5-methoxymethyl-2,3-dipropargyloxybenzene according to Procedure (e):

A mixture of 3-chloro-4,5-dipropargyloxybenzyl alcohol (1.00 g), potassium hydroxide (1.00 g), iodomethane (1.00 g) and tetra-n-butylammonium bromide (1.00 g) in tetrahydrofuran (30 ml) was stirred at room temperature for 2 hours, poured into ice-water and extracted with ethyl acetate. The extract was washed with water, dried over magnesium sulfate and concentrated under reduced pressure. The residue was purified by silica gel column chromatography using toluene as an eluent to give 1-chloro-5-methoxymethyl-2,3-dipropargyloxybenzene (0.95 g). $n_D^{23.0}$ 1.5450.

EXAMPLE 7

Preparation of 3-chloro-4,5-dipropargyloxybenzophenone according to Procedure (f):

A mixture of diethyl 3-chloro-4,5-dipropargyloxybenzomalonate (5.00 g) in acetic acid (30 ml), sulfuric acid (4 ml) and water (20 ml) was stirred under reflux for 2 hours, poured into ice-water and extracted with ethyl acetate. The extract was washed with potassium carbonate solution and water, dried over magnesium sulfate and concentrated under reduced pressure. The residue was purified by silica gel column chromatography using toluene as an eluent to give 3-chloro-4,5-dipropargyloxybenzophenone (2.45 g). m.p., 88.4°–89° C.

In the same manner as above, the dipropargyloxybenzene compounds (I) of the invention as shown in Table 1 can be prepared.

TABLE 1

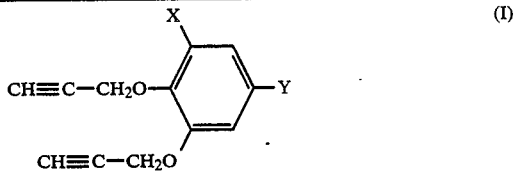

(I)

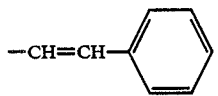

| Compound No. | X | Y | Physical constant |
|---|---|---|---|
| 1 | Cl | CH₃ | ¹H-NMR δ TMS (CDCl₃) ppm: 6.70–6.90 (2H), 4.68 (d, 4H), 2.40–2.60 (2H), 2.25 (s, 3H) |
| 2 | Cl | —OCH₃ | ¹H-NMR δ TMS (CDCl₃) ppm: 6.50 (s, 2H), 4.60–4.80 (4H), 3.72 (s, 3H), 2.42–2.62 (2H) |
| 3 | Cl | —OCH₂CH=CH₂ | $n_D^{25.5}$ 1.5492 |
| 4 | Cl | —OCH₂C≡CH | $n_D^{25.5}$ 1.5565 |
| 5 | Cl | —C₂H₅ | $n_D^{19.0}$ 1.4330 |
| 6 | Cl | —C₃H₇(n) | $n_D^{22.0}$ 1.5368 |
| 7 | Cl | —C₄H₉(n) | $n_D^{22.0}$ 1.5285 |
| 8 | Cl | —CH=CH₂ | ¹H-NMR δ TMS (CDCl₃) ppm: 6.90 (d, 1H), 7.00³ (d, 1H), 5.00–6.80 (m, 3H), 4.70 (d, 4H), 2.35–2.50 (m, 2H) |
| 9 | Cl | —CH=CHCH₃ | ¹H-NMR δ TMS (CDCl₃) ppm: 6.80 (d, 1H), 6.90³ (d, 1H), 6.10–6.20 (m, 2H), 4.70 (d, 4H), 2.40–2.55 (m, 2H), 1.80 (d, 3H) |
| 10 | Cl | —CH=CHC₂H₅ | $n_D^{25.5}$ 1.5602 |
| 11 | Cl | —CH=CH—C₆H₅ | m.p. 67.6–69.6° C. |

TABLE 1-continued $$\text{(I)}$$

Structure: benzene ring with X at one position, Y at another, and two CH≡C—CH₂O— groups.

| Compound No. | X | Y | Physical constant |
|---|---|---|---|
| 12 | Cl | —OC$_2$H$_5$ | m.p. 72.5–73.5° C. |
| 13 | Cl | —OC$_3$H$_7$(n) | $^1$H-NMR δ TMS (CDCl$_3$) ppm: 6.45 (s, 2H), 4.60–4.80 (m, 4H), 3.78 (t, 2H), 2.50–2.70 (m, 2H), 1.50–2.10 (m, 2H), 0.80–1.40 (t, 3H) |
| 14 | Cl | —OCH$_2$OCH$_3$ | $^1$H-NMR δ TMS (CDCl$_3$) ppm: 6.80 (2H), 5.05 (s, 2H), 4.60–4.80 (4H), 3.40 (s, 3H), 2.50–2.70 (m, 2H) |
| 15 | Cl | —OCH$_2$CH=CHCl | $n_D^{24.5}$ 1.5619 |
| 16 | Cl | —OCH$_2$—C(Cl)=CH$_2$ | $n_D^{26.5}$ 1.5546 |
| 17 | Cl | —OCH$_2$—C(=O)CH$_3$ | m.p. 74.5° C. |
| 18 | Cl | —OCH$_2$C≡N | $n_D^{26.5}$ 1.5522 |
| 19 | Cl | —OCH$_2$—C(=O)—OH | m.p. 80–86° C. |
| 20 | Cl | —OCH$_2$—C(=O)—NH—C$_3$H$_7$(n) | m.p. 121.5–122° C. |
| 21 | Cl | —OCH$_2$—C$_6$H$_5$ | $n_D^{22.0}$ 1.5808 |
| 22 | Cl | —OCH$_2$CH$_2$F | $n_D^{22.0}$ 1.5416 |
| 23 | Cl | —CH$_2$OCH$_3$ | $n_D^{23.0}$ 1.5450 |
| 24 | Cl | —CH$_2$—O—CH$_2$CH=CH$_2$ | $^1$H-NMR δ TMS (CDCl$_3$) ppm: 6.88–7.05 (2H), 5.00–6.20 (m, 3H), 4.70 (d, 4H), 4.32 (s, 2H), 4.00 (d, 2H), 2.40–2.60 (2H) |
| 25 | Cl | —CH$_2$—O—CH$_2$C≡CH | $^1$H-NMR δ TMS (CDCl$_3$) ppm: 6.95–7.10 (2H), 4.75 (d, 4H), 4.52 (s, 2H), 4.15 (d, 2H), 2.45–2.60 (2H) |
| 26 | Cl | —CH=CH—CN | m.p. 110–111° C. |
| 27 | Cl | —CH=CH—COOCH$_3$ | m.p. 92.5–93.5° C. |
| 28 | Cl | —CH=CH—COCH$_3$ | m.p. 92–93° C. |
| 29 | Cl | —CH=N—N(CH$_3$)$_2$ | $n_D^{11.0}$ 1.5920 |
| 30 | Cl | —CH=N—C$_6$H$_5$ | $n_D^{23.0}$ 1.5890 |
| 31 | Cl | —C(=O)—CH$_3$ | m.p. 88.4–89° C. |
| 32 | Br | —OCH$_3$ | m.p. 83.7–84° C. |
| 33 | Cl | —OCH$_2$CH$_2$Cl | $n_D^{22.5}$ 1.5440 |

In the practical use of the dipropargyloxybenzene compounds (I) as fungicides, they may be applied as such or in a formulation form such as dusts, wettable powders, oil sprays, emulsifiable concentrates, tablets, granules, fine granules, aerosols or flowables. Such preparation form can be formulated in a conventional manner by mixing at least one of the dipropargyloxybenzene compounds (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are botanical materials (e.g. flour, tobacco stalk powder, soybean powder, walnut-shell powder, vegetable powder, saw dust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include casein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), tricresyl phosphate (TCP), tolu oil, epoxydized oil, various surfactants, various fatty acids and their esters, etc.

The foregoing formulations generally contain at least one of the dipropargyloxybenzene compounds (I) in a concentration of about 1 to 95% by weight, preferably of 2.0 to 80% by weight. By using the formulations, the dipropargyloxybenzene compounds (I) are generally applied in such amounts as 2 to 100 g per 10 are.

When only the drug-resistant strains of phytopathogenic fungi are present, the dipropargyloxybenzene compounds (I) may be used alone. However, when the drug-sensitive strains are present together with the drug-resistant strains, their alternate use with benzimidazole, thiophanate and/or cyclic imide fungicides or their combined use with benzimidazole, thiophanate and/or cyclic imide fungicides is favorable. In such alternate or combined use, each active ingredient may be employed as such or in conventional agricultural formulation forms. In case of the combined use, the weight proportion of the dipropargyloxybenzene compound (I) and the benzimidazole, thiophanate and/or cyclic imide fungicide may be from about 1:0.1 to 1:10.0.

Typical examples of the benzimidazole, thiophanate and cyclic imide fungicides which are commercially available are shown in Table 2.

TABLE 2

| Compound | Structure | Name |
|---|---|---|
| A | 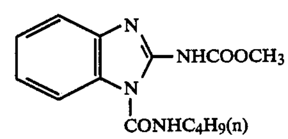 | Methyl 1-(butylcarbamoyl)benzimidazol-2-yl-carbamate |
| B | 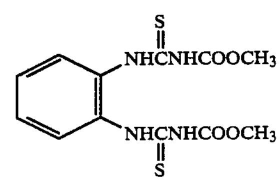 | 1,2-Bis(3-methoxycarbonyl-2-thioureido)benzene |
| C | 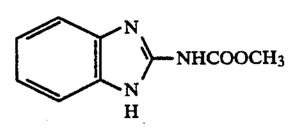 | Methyl benzimidazol-2-yl-carbamate |
| D | 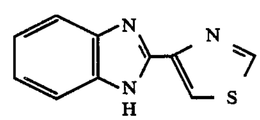 | 2-(4-Thiazolyl)benzimidazole |
| E | 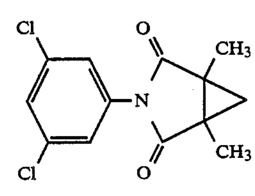 | N—(3',5'-Dichlorophenyl)-1,2-dimethylcyclopropane-1,2-dicarboximide |

TABLE 2-continued

| Compound | Structure | Name |
|---|---|---|
| F | (3',5'-dichlorophenyl with N-acetyl imidazolidine-2,4-dione bearing N—C(=O)—NHCH(CH$_3$)$_2$) | 3-(3',5'-Dichlorophenyl)-1-isopropyl-carbamoylimidazolidin-2,4-dione |
| G | (3',5'-dichlorophenyl-N-oxazolidinedione with CH=CH$_2$ and CH$_3$ substituents) | 3-(3',5'-Dichlorophenyl)-5-methyl-5-vinyloxazolidin-2,4-dione |
| H | (3',5'-dichlorophenyl-N-oxazolidinedione with COOC$_2$H$_5$ and CH$_3$ substituents) | Ethyl (RS)-3-(3',5'-dichlorophenyl)-5-methyl-2,4-dioxo-oxazolidine-5-carboxylate |

The dipropargyloxybenzene compounds (I) may be also used in admixture with other fungicides, herbicides, insecticides, miticides, fertilizers, etc.

When the dipropargyloxybenzene compounds (I) are used as fungicides, they may be applied in such amounts as 2 to 100 grams per 10 are. However, this amount may vary depending upon formulation forms, application times, application methods, application sites, diseases, crops and so on, and therefore, they are not limited to particular amounts.

Some practical embodiments of the fungicidal composition according to the invention are illustratively shown in the following Examples wherein % and part(s) are by weight.

FORMULATION EXAMPLE 1

Two parts of each of Compound Nos. 1 to 33, 88 parts of kaolin clay and 10 parts of talc are thoroughly pulverized and mixed together to obtain a dust formulation containing 2% of the active ingredient.

FORMULATION EXAMPLE 2

Ten parts of each of Compound Nos. 1 to 33, 1 part of polyoxyethylene styrylphenyl ether as an emulsifier and 89 parts of water are mixed together to obtain an emulsifiable concentrate formulation containing 10% of the active ingredient.

FORMULATION EXAMPLE 3

Eighty parts of each of Compound Nos. 1 to 33, 10 parts of cyclohexanone and 10 parts of polyoxyethylene alkylaryl ether as an emulsifier are mixed together to obtain an emulsifiable concentrate formulation containing 80% of the active ingredient.

FORMULATION EXAMPLE 4

Two parts of each of Compound Nos. 1 to 33, 88 parts of clay and 10 parts of talc are thoroughly pulverized and mixed together to obtain a dust formulation containing 2% of the active ingredient.

FORMULATION EXAMPLE 5

One part of each of Compound Nos. 1 to 33, 1 part of Compound A, 88 parts of clay and 10 parts of talc are thoroughly pulverized and mixed together to obtain a dust formulation containing 2 parts of the active ingredient.

FORMULATION EXAMPLE 6

Twenty parts of each of Compound Nos. 1 to 33, 10 parts of Compound F, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder composition containing 30% of the active ingredient.

FORMULATION EXAMPLE 7

Ten parts of each of Compound Nos. 1 to 33, 40 parts of Compound B, 45 parts of diatomaceous earth, 2.5 parts of calcium alkylbenzenesulfonate as a wetting agent and 2.5 parts of calcium ligninsulfonate as a dispersing agent are mixed while being powdered to obtain a wettable powder composition containing 50% of the active ingredient.

FORMULATION EXAMPLE 8

Five parts of each of Compound Nos. 1 to 33, 5 parts of Compound C, 80 parts of cyclohexanone and 10 parts of polyoxyethylene alkylaryl ether as an emulsifier are mixed together to obtain an emulsifiable concentrate formulation containing 10% of the active ingredient.

Typical test data indicating the excellent fungicidal activity of the dipropargyloxybenzene compounds (I) are shown below.

EXPERIMENT 1

Preventive effect on gray mold of cucumber (*Botrytis cinerea*):

A plastic pot of 90 ml volume was filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 30 ml per pot. After air-drying, the seedlings were inoculated with mycelial disks (5 mm in diameter) of the drug-resistant or drug-sensitive strain of *Botrytis cinerea* by putting them on the leaf surfaces. After the plants were infected by incubating under high humidity at 20° C. for 3 days, the rates of disease severity were observed. The degree of damage was determined in the following manner, and the results are shown in Table 3.

The leaves examined were measured for a percentage of infected area and classified into the corresponding disease indices, 0, 0.5, 1, 2, 4:

| Disease index | Percentage of infected area |
| --- | --- |
| 0 | No infection |
| 0.5 | Infected area of less than 5% |
| 1 | Infected area of not less than 5% but less than 20% |
| 2 | Infected area of not less than 20% but less than 50% |
| 4 | Infected area of not less than 50% |

The disease severity was calculated according to the following equation:

$$\text{Disease severity (\%)} = \frac{\Sigma\{(\text{Disease index}) \times (\text{Number of leaves})\}}{4 \times (\text{Total number of leaves examined})} \times 100$$

The prevention value was calculated according to the following equation:

$$\text{Prevention value (\%)} = 100 - \frac{(\text{Disease severity in treated plot})}{(\text{Disease severity in untreated plot})} \times 100$$

TABLE 3

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 200 | 100 | 0 |
| 2 | 200 | 100 | 0 |
| 3 | 200 | 100 | 0 |
| 4 | 200 | 100 | 0 |
| 5 | 200 | 100 | 0 |
| 6 | 200 | 100 | 0 |
| 7 | 200 | 100 | 0 |
| 8 | 200 | 100 | 0 |
| 9 | 200 | 100 | 0 |
| 10 | 200 | 93 | 0 |
| 11 | 200 | 93 | 0 |
| 12 | 200 | 100 | 0 |
| 13 | 200 | 100 | 0 |
| 14 | 200 | 100 | 0 |
| 15 | 200 | 100 | 0 |
| 16 | 200 | 100 | 0 |
| 17 | 200 | 100 | 0 |
| 18 | 200 | 88 | 0 |
| 19 | 200 | 75 | 0 |
| 20 | 200 | 100 | 0 |
| 21 | 200 | 91 | 0 |
| 22 | 200 | 100 | 0 |
| 23 | 200 | 100 | 0 |
| 24 | 200 | 97 | 0 |
| 25 | 200 | 97 | 0 |
| 26 | 200 | 100 | 0 |
| 27 | 200 | 94 | 0 |
| 28 | 200 | 94 | 0 |
| 29 | 200 | 100 | 0 |
| 30 | 200 | 97 | 0 |
| 31 | 200 | 100 | 0 |
| 32 | 200 | 75 | 0 |
| A | 200 | 0 | 100 |
| B | 200 | 0 | 100 |
| C | 200 | 0 | 100 |
| D | 200 | 0 | 100 |

EXPERIMENT 2

Fungitoxic activity against *Pseudocercosporella herpotrichoides*:

Test compounds were each dissolved in dimethylsulfoxide to make desired concentrations, mixed with melted PDA (potato dextrose agar) and poured into petri dishes. Spore suspensions of *Pseudocercosporella herpotrichoides* were inoculated on the solidified plates, and incubation was performed at 23° C. for 7 days. The evaluation of the fungitoxic activity was made according to the degree of fungal growth on the following criteria:

−: no fungal growth was observed
±: slight fungal growth was observed
+: fungal growth less than that in the untreated plot was observed
++: fungal growth equal to that in the untreated plot was observed The results are shown in Table 4.

TABLE 4

| Compound No. | Concentration of active ingredient (ppm) | Fungitoxic activity when inoculated with drug-resistant strain | Fungitoxic activity when inoculated with drug-sensitive strain |
| --- | --- | --- | --- |
| 1 | 100 | − | −∼± |
|   | 10 | − | ++ |
|   | 1 | − | ++ |
|   | 0.1 | − | ++ |
| 2 | 100 | − | −∼± |
|   | 10 | − | ++ |
|   | 1 | − | ++ |
|   | 0.1 | − | ++ |
| 3 | 100 | − | −∼± |
|   | 10 | − | ++ |
|   | 1 | − | ++ |
|   | 0.1 | − | ++ |
| 4 | 100 | − | − |
|   | 10 | − | ++ |
|   | 1 | − | ++ |
|   | 0.1 | − | ++ |
| 12 | 100 | − | ++ |
|   | 10 | − | ++ |
|   | 1 | − | ++ |
|   | 0.1 | − | ++ |
| 13 | 100 | − | ++ |
|   | 10 | − | ++ |
|   | 1 | − | ++ |
|   | 0.1 | −∼± | ++ |
| 14 | 100 | − | ++ |
|   | 10 | − | ++ |
|   | 1 | − | ++ |
|   | 0.1 | − | ++ |
| 15 | 100 | − | ++ |
|   | 10 | − | ++ |
|   | 1 | − | ++ |
|   | 0.1 | ± | ++ |

TABLE 4-continued

| Compound No. | Concentration of active ingredient (ppm) | Fungitoxic activity when inoculated with drug-resistant strain | Fungitoxic activity when inoculated with drug-sensitive strain |
|---|---|---|---|
| 19 | 100 | − | ++ |
|    | 10  | − | ++ |
|    | 1   | ± | ++ |
|    | 0.1 | ++ | ++ |
| 20 | 100 | − | ++ |
|    | 10  | − | ++ |
|    | 1   | − | ++ |
|    | 0.1 | ++ | ++ |
| 23 | 100 | − | ++ |
|    | 10  | − | ++ |
|    | 1   | − | ++ |
|    | 0.1 | − | ++ |
| 24 | 100 | − | ++ |
|    | 10  | − | ++ |
|    | 1   | − | ++ |
|    | 0.1 | ± | ++ |
| 25 | 100 | − | ++ |
|    | 10  | − | ++ |
|    | 1   | − | ++ |
|    | 0.1 | − | ++ |
| 26 | 100 | − | ++ |
|    | 10  | − | ++ |
|    | 1   | − | ++ |
|    | 0.1 | − | ++ |
| 27 | 100 | − | ++ |
|    | 10  | − | ++ |
|    | 1   | − | ++ |
|    | 0.1 | − | ++ |
| 28 | 100 | − | ++ |
|    | 10  | − | ++ |
|    | 1   | − | ++ |
|    | 0.1 | − | ++ |
| 29 | 100 | − | ++ |
|    | 10  | − | ++ |
|    | 1   | − | ++ |
|    | 0.1 | + | ++ |
| 30 | 100 | − | ++ |
|    | 10  | − | ++ |
|    | 1   | − | ++ |
|    | 0.1 | + | ++ |
| A  | 100 | + | ± |
|    | 10  | ++ | ± |
|    | 1   | ++ | ± |
|    | 0.1 | ++ | + |

EXPERIMENT 3

Preventive effect on gray mold of tomato (*Botrytis cinerea*):

A plastic pot of 90 ml volume was filled with sandy soil, and seeds of tomato (var: Fukuju No. 2) were sowed therein. Cultivation was carried out in a greenhouse for 4 weeks. Onto the resulting seedlings at the 4-leaf stage, the test compound(s) formulated in emulsifiable concentrate or wettable powder and diluted with water were sprayed at a rate of 30 ml per pot. Then, the seedlings were inoculated with a mixed spore suspension of the drug-resistant and drug-sensitive strain of *Botrytis cinerea* by spraying and placed at 20° C. in a room of high humidity for 5 days. The degree of damage was determined in the same manner as in Experiment 1, and the results are shown in Table 5.

TABLE 5

| Compound No. | Concentration of active ingredient (ppm) | Prevention value (%) |
|---|---|---|
| 1 | 100 | 30 |
| 1 | 20  | 0 |
| 2 | 100 | 32 |
| 2 | 20  | 0 |
| 4 | 100 | 28 |
| 4 | 20  | 0 |
| 5 | 100 | 36 |
| 5 | 20  | 0 |
| 8 | 100 | 34 |
| 8 | 20  | 0 |
| 13 | 100 | 28 |
| 13 | 20  | 0 |
| 14 | 100 | 30 |
| 14 | 20  | 0 |
| 15 | 100 | 32 |
| 15 | 20  | 0 |
| 16 | 100 | 28 |
| 16 | 20  | 0 |
| 22 | 100 | 30 |
| 22 | 20  | 0 |
| A | 100 | 46 |
| A | 20  | 18 |
| B | 100 | 50 |
| B | 20  | 24 |
| C | 100 | 48 |
| C | 20  | 22 |
| D | 100 | 44 |
| D | 20  | 16 |
| E | 100 | 48 |
| E | 20  | 20 |
| F | 500 | 44 |
| F | 100 | 16 |
| G | 100 | 40 |
| G | 20  | 18 |
| H | 500 | 42 |
| H | 100 | 10 |
| 1 + A | 10 + 20 | 100 |
| 1 + B | 10 + 20 | 100 |
| 1 + C | 10 + 20 | 100 |
| 1 + D | 10 + 20 | 100 |
| 2 + E | 10 + 20 | 100 |
| 2 + F | 10 + 20 | 100 |
| 2 + G | 10 + 20 | 100 |
| 2 + H | 10 + 20 | 100 |
| 4 + A | 10 + 20 | 100 |
| 5 + B | 10 + 20 | 100 |
| 8 + C | 10 + 20 | 100 |
| 13 + D | 10 + 20 | 100 |
| 14 + E | 10 + 20 | 100 |
| 15 + F | 10 + 20 | 100 |
| 16 + G | 10 + 20 | 100 |
| 22 + H | 10 + 20 | 100 |

What is claimed is:

1. A compound of the formula:

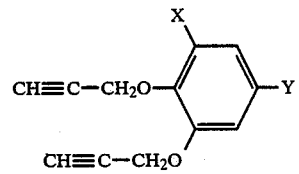

wherein X is a chlorine atom and Y is a methyl group.

2. A fungicidal composition which comprises as an active ingredient of fungicidally effective amount of the compound of claim 1 and an inert carrier or diluent.

3. The fungicidal composition according to claim 2, which further comprises as an additional active ingredient(s) at least one of benzimidazole, thiophanate and cyclic imide fungicides.

4. The fungicidal composition according to claim 3, wherein the benzimidazole, thiophanate or cyclic imide fungicide is methyl 1-(butylcarbamoyl)benzimidazol-2-yl-carbamate, 2-(2-furyl)benzimidazole, 2-(4- thiazolyl)benzimidazole, methyl benzimidazol-2-ylcarbamate, 1,2-bis(3-methoxycarbonyl-2-thioureido)benzene, 1,2-bis(3-ethoxycarbonyl-2-thioureido)benzene, 2-(O,S-dimethylphosphorylamino)-1-(3'-methoxycarbonyl-2'-thioureido)benzene or 2-(O,O-dimethylthiophosphorylamino)-1-(3'-methoxycarbonyl-2'-thioureido)benzene and the cyclic imide fungicide is 3-(3',5'-dichlorophenyl)-1,2-dimethylcyclopropane-1,2-dicarboximide, 3-(3',5'-dichlorophenyl)-1-isopropylcarbamoylimidazolidine-2,4-dione, 3-(3',5'-dichlorophenyl)-5-methyl-5-vinyloxazoline-2,4-dione or ethyl (RS)-3-(3',5'-dichlorophenyl)-5-methyl-2,4-dioxooxazolidine-5-carboxylate.

5. The fungicidal composition according to claim 2, which is effective for plant pathogenic fungi having a drug-resistance.

6. A method for controlling plant pathogenic fungi which comprises applying a fungicidally effective amount of the compound of claim 1 to plant pathogenic fungi.

7. The method according to claim 6, wherein the plant pathogenic fungi is a drug-resistant strain.

8. A method for controlling plant pathogenic fungi which comprises applying a fungicidally effective amount of a mixture of the compound of claim 1 and a benzimidazole, thiophanate or cyclic imide fungicide to plant pathogenic fungi.

* * * * *